United States Patent [19]

Hirsch

[11] Patent Number: 4,477,256
[45] Date of Patent: Oct. 16, 1984

[54] SURGICAL SPONGE

[76] Inventor: Win Hirsch, 30 Sylvia Rd., Plainview, N.Y. 11803

[21] Appl. No.: 585,838

[22] Filed: Mar. 2, 1984

Related U.S. Application Data

[63] Continuation of Ser. No. 348,037, Feb. 11, 1982, abandoned.

[51] Int. Cl.³ .............................................. A61F 13/00
[52] U.S. Cl. .................................. 604/362; 604/358; 604/366; 604/381; 604/384
[58] Field of Search .............. 604/358, 362, 366, 381, 604/384, 13, 15, 904

[56] References Cited

U.S. PATENT DOCUMENTS

| | | | |
|---|---|---|---|
| 1,208,313 | 12/1916 | Haydon | 128/170 |
| 1,533,272 | 4/1925 | Respess | 128/170 |
| 2,972,350 | 2/1961 | Deker | 604/362 |
| 3,566,871 | 3/1971 | Richter et al. | 604/362 |
| 3,911,922 | 10/1975 | Kliger | 604/362 |
| 3,976,075 | 8/1976 | Chinai et al. | 604/904 |
| 4,205,680 | 6/1980 | Marshall | 604/362 |
| 4,244,369 | 1/1981 | McAvinn et al. | 604/362 |

FOREIGN PATENT DOCUMENTS 646560  10/1935  Fed. Rep. of Germany ...... 433/136

OTHER PUBLICATIONS

Distributor Price List, Chaston Medical and Surgical Products, May 10, 1980.
Chaston Hospital Catalog, p. 8.

*Primary Examiner*—C. Fred Rosenbaum
*Assistant Examiner*—Gene B. Kartchner
*Attorney, Agent, or Firm*—Eugene E. Geoffrey, Jr.

[57] ABSTRACT

A surgical sponge principally for blunt dissection formed of an elongated strip of absorbent material such as woven cotton or the like rolled to form a cylindrical structure. At least the outer layer of the roll is adhesively secured to the roll to prevent unwinding and a radiation opaque material is contained within the sponge and is preferably intermixed with the adhesive.

11 Claims, 7 Drawing Figures

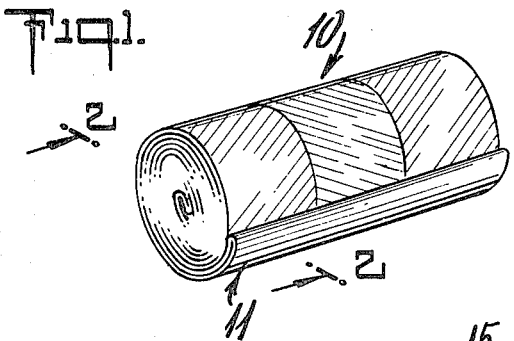
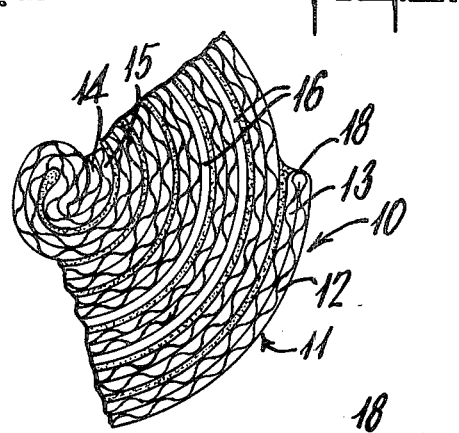
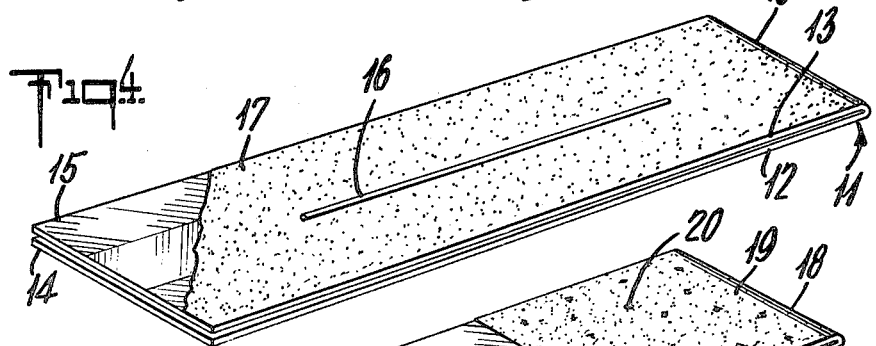
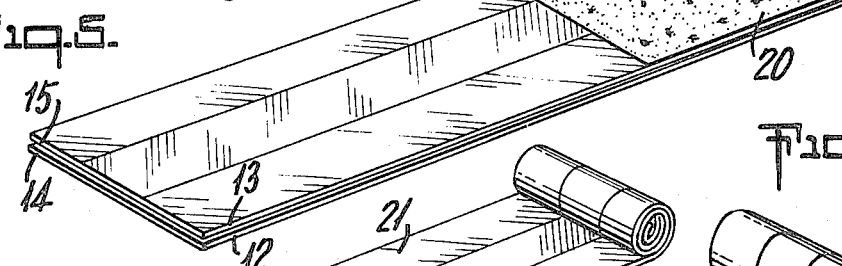
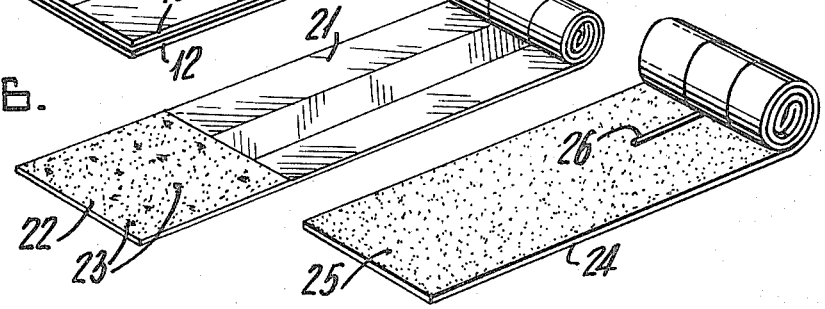

SURGICAL SPONGE

This is a continuation of Ser. No. 348,037 dated Feb. 11, 1982 which is now abandoned.

This invention relates to surgical sponges and more specifically to a novel and improved sponge embodying X-ray opaque material characterized by its simplicity, ease of manufacture and relatively low cost.

Small surgical sponges for blunt dissection generally known in the art as Kittner sponges are customarily formed of a narrow strip of woven cotton tightly rolled by hand and sewn to form a cylindrical structure. A piece of X-ray opaque thread is included within the rolled cotton strip to facilitate location. In order to avoid frayed end portions, each strip of cotton is generally folded upon itself and then rolled with the free ends at the center of the roll. The folded outer end must then be hand sewn to complete the sponge with the ends of the thread being suitably knotted to prevent loosening of the stitches.

This invention overcomes the difficulties heretofore encountered in the manufacture of Kittner sponges and provides a novel and improved sponge which can be readily fabricated by automatic machinery thus avoiding expensive hand operations and providing greater uniformity in size and density. X-ray opaque material may be automatically included in the sponge and at the same time avoid bleeding or deterioration.

Another object of the invention resides in the provision of a novel and improved sponge which can be fabricated free from contamination resulting from hand fabrication and fraying of the absorbent material and which at the same time can be produced more rapidly with negligible variation in absorbent characteristics and at a reduced cost.

Still another object of the invention resides in the provision of a novel and improved sponge, particularly useful for blunt dissection wherein the surface contour of the woven cotton strip, whether of conventional weave or chevron weave, as illustrated in the drawings by the alternate cross hatching is essentially retained to provide increased friction with tissues being separated by the sponge and at the same time provides a sponge that will more readily retain its shape and configuration.

Still another object of the invention resides in the provision of a novel and improved surgical sponge and method for the manufacture thereof. The above and other objects and advantages of the invention will become more apparent from the following description and accompanying drawings forming part of this application.

IN THE DRAWINGS

FIG. 1 is a perspective view of a surgical sponge in accordance with one embodiment of the invention;

FIG. 2 is an enlarged cross sectional view of a fragmentary portion of FIG. 1 taken in the direction of the line 2—2 thereof;

FIG. 3 is an end view of a modified embodiment of a surgical sponge in accordance with the invention;

FIG. 4 is a perspective view of a step in the manufacture of one embodiment of the invention wherein the absorbent strip is folded preparatory to the rolling operation;

FIG. 5 is a perspective view of a step in the manufacture of another embodiment of the invention preparatory to the rolling operation;

FIG. 6 is a perspective view of a step in the manufacture of still another embodiment of the invention; and FIG. 7 is a perspective view of a still further embodiment of the invention.

Surgical sponges generally known in the art as the Kittner sponge for use in blunt dissection are fabricated from an absorbent strip of material formed of woven cotton or the like. The strip is folded upon itself and then formed into a roll with the free ends of the strip at the center of the roll. During the rolling operation, a thread containing barium sulfate or other suitable X-ray opaque material is included between the layers and upon completion of the rolling operation the folded end portion is then sewn in place. The ends of the thread must be carefully knotted to prevent any possibility of the loosening of the stitches. Sponges of this type are normally approximately one-half inch long and one-quarter inch in diameter through it is apparent that the sponge can be made of any desired size.

Known surgical sponges of the type described above present numerous difficulties which include in addition to the relatively high cost occasioned by hand operations, the danger that the threads will loosen or even break and the possibility of contamination and absorption of foreign matter. While sterilization will normally inactivate contaminants, it will have little if any affect on foreign matter which is not only undesirable but may present serious problems depending upon the nature thereof. On the other hand, the sponge in accordance with this invention can be readily fabricated by automatic machinery which not only reduces the cost of the item but produces sponges having more uniform physical size and characteristics and the reduction if not complete elimination of contamination and foreign matter.

One form of sponge in accordance with the invention is illustrated in FIGS. 1 and 2 and designated generally by the numeral 10. The sponge is formed of a strip of material generally denoted by the numeral 11 which is folded upon itself preparatory to rolling as shown in FIG. 4 to provide layers 12 and 13. The free ends 14 and 15 of the strip of material 11 form the start of the roll and during the course of the rolling operation, a thin thread 16 of X-ray opaque material is rolled simultaneously with the strip 11 so that it is securely contained within the roll. One form of thread which has been found to be satisfactory consists of a filament formed of vinyl-plastic containing an adequate amount of barium sulfate. In the instant embodiment of the invention, a layer of adhesive 17 is applied to the layer 13 of the folded strip 11 preparatory to the rolling operation with the result that successive overlying turns are secured one to the others and the folded end 18 is firmly secured in position. The adhesive 17 may take any suitable form provided however that it is of a non-toxic nature. For instance, it may have a consistency to permit application by spraying, brushing or rolling or it may be in the form of a thin strip which is placed in overlying relationship with the layer 13 throughout part or all of its length. The adhesives may be self-setting, a hot melt, thermo-setting or thermo-plastic. In the latter case, a heat sealable vinyl-plastic has been found to be satisfactory and the plastic may be either in sheet form which can be rolled with the absorbent tape or may be applied to the tape prior to rolling. If desired, an adhesive may also be disposed between the layers 12 and 13.

The use of adhesives between the successive layers of the cotton strip used to form the sponge in accordance with the invention will function to decrease the absorbent characteristics of the sponge. However, since the sponge is used principally for blunt dissection, some reduction in absorbency has been found most desirable since the sponge will retain its stiffness and configuration and thus be far more effective as a blunt dissector.

A modified form of the invention illustrated in FIGS 1, 3 and 4 is shown in FIG. 5 wherein like numerals have been utilized to denote corresponding elements. In this form of the invention, the absorbent tape is folded upon itself to form the layers 12 and 13 and a layer of adhesive 19 is applied to part or all of the surface of the tape 13. The adhesive 19 in this form of the invention includes an adequate quantity of barium sulfate denoted by the numeral 20. The barium sulfate is combined with the adhesive whether it be in sheet form or a viscous liquid and thus avoids necessity for including an X-ray opaque thread 16. As mentioned in connection with the previous embodiment of the invention, a layer of adhesive containing barium sulfate may also be interposed between the layers 12 and 13 prior to the rolling operation. With the utilization of the barium sulfate as part of the adhesive and through the utilization of an adequate quantity of the adhesive, an X-ray photograph will provide a clearer image of the actual shape and size of the sponge.

FIG. 3 illustrates a modified embodiment of the invention which utilizes a reversal of the rolling procedure illustrated in connection with FIGS. 1 and 2. In this form of the invention, generally denoted by the numeral 10', the absorbent tape is folded upon itself and the folded end portion 18' is disposed at the center of the roll while the free end portions 14' and 15' are disposed at the outer surface of the roll. When rolling the sponge in the manner ilustrated in FIG. 3, a layer of adhesive such as the adhesive 17 or 19 would be disposed between the layers 12' and 13' and specifically at least adjoining the free ends 14' and 15'. A layer of adhesive would also be applied at least to the free end portion of the layer 13'. As in the previous embodiment of the invention, the adhesive carries an X-ray opaque material such as barium sulfate or the like.

A further modification of the invention is illustrated in FIG. 6. In this form of the invention, the absorbent tape 21 is in the form of a single layer having adhesive 22 containing radiation opaque particles 23 on one end thereof as illustrated or throughout the entire length of the tape. The tape is then rolled, the start of which is illustrated in the figure so that the resultant structure will have a configuration similar to that illustrated in FIG. 1. As in the case of the previous embodiments of the invention, the adhesive may be in the form of a self-adhering viscous liquid applied by a spray, brush or roller or may be in the form of a tape which is rolled simultaneously with the rolling of the absorbent tape 21. In the event a heat sealing adhesive is utilized, the rolled sponge would be subjected to a suitable source of heat while retained in the rolled position to activate the adhesive in order to secure the end of the absorbent tape securely to the completed roll.

The embodiment of the invention shown in FIG. 7 differs from the preceding embodiments in that the absorbent layer 24 is a single ply and an adhesive whether in liquid or tape form extends throughout the entire length of the layer 24 to control cut edges and prevent fraying. An X-ray opaque thread 26, which is the equivalent of the thread 16 as described in connection with FIGS. 1, 2 and 4, is disposed centrally of the layer 24 and is incorporated within the sponges during the rolling process. As in the preceding embodiments of the invention, any suitable non-toxic adhesive may be used and in the case of heat-sealing or thermo-plastic adhesives, the completed sponge is subjected to a suitable source of heat to set the adhesive.

While only certain embodiments of the invention have been illustrated and described, it is understood that alterations, changes and modifications may be made without departing from the true scope and spirit thereof.

What is claimed is:

1. A surgical sponge of the blunt dissection type comprising an elongated strip of absorbent material rolled to form an essentially cylindrical roll with successive overlying layers and having an outer layer including the terminal end portion with the length of the structure being approximately equal to the width of the strip, a continuous coating of adhesive material permanently securing at least said outer layer throughout its width to said roll and a radiation opaque material within said roll.

2. A surgical sponge of the blunt dissection type according to claim 1 wherein said adhesive is a self-setting viscous material.

3. A surgical sponge of the blunt dissection type according to claim 1 wherein said adhesive is a thermoplastic material.

4. A surgical sponge of the blunt dissection type according to claim 1 wherein said adhesive includes a radiation opaque material carried thereby.

5. A surgical sponge of the blunt dissection type according to claim 1 wherein said strip of adsorbent material is folded upon itself to form overlying laminations prior to being rolled to form an essentially cylindrical roll and an adhesive between at least the end portions of said overlying laminations.

6. A surgical sponge of the blunt dissection type according to claim 6 wherein the adjoining ends of said strip are disposed at the center of said roll.

7. A surgical sponge of the blunt dissection type according to claim 6 wherein the folded end portion is disposed at the center of said roll.

8. A surgical sponge of the blunt dissection type according to claim 1 wherein said strip includes a layer of adhesive extending throughout substantially the entire length and width thereof and a radiation opaque material disposed within said cylindrical structure.

9. A surgical sponge of the blunt dissection type comprising an elongated strip of absorbent material folded lengthwise upon itself to provide overlying laminations and then rolled to form an essentially cylindrical roll having successive overlying layers and including an outer terminal end portion with the length of the structure being approximately equal to the width of the strip, and a continuous coating of adhesive permanently securing each successive layer throughout its length and width to the underlying layer and a radiation opaque material within said roll.

10. A surgical sponge of the blunt dissection type according to claim 9 wherein said folded end portion is disposed at the center of said roll and an adhesive is disposed between at least the overlying end portions of the laminations of said folded strip.

11. A surgical sponge of the blunt dissection type according to claim 9 wherein the free end portions of the folded strip are disposed at the center of the roll and an adhesive is disposed at least between the laminations adjoining the folded end portion.

* * * * *